United States Patent
Li et al.

(10) Patent No.: US 9,719,082 B2
(45) Date of Patent: *Aug. 1, 2017

(54) SUBSTRATES AND ASSOCIATED METHODS FOR ELUTION OF NUCLEIC ACIDS

(71) Applicant: General Electric Company, Schenectady, NY (US)

(72) Inventors: Bing Li, Clifton Park, NY (US); Gregory Andrew Grossmann, Halfmoon, NY (US); David Roger Moore, Rexford, NY (US)

(73) Assignee: General Electric Company, Niskayuna, NY (US)

( * ) Notice: Subject to any disclaimer, the term of this patent is extended or adjusted under 35 U.S.C. 154(b) by 399 days.

This patent is subject to a terminal disclaimer.

(21) Appl. No.: 14/068,532

(22) Filed: Oct. 31, 2013

(65) Prior Publication Data

US 2015/0118683 A1   Apr. 30, 2015

(51) Int. Cl.
   *C07H 21/00* (2006.01)
   *C12N 15/10* (2006.01)

(52) U.S. Cl.
   CPC ................. *C12N 15/1006* (2013.01)

(58) Field of Classification Search
   CPC .................................................. C12N 15/1006
   USPC ........................................................ 536/25.42
   See application file for complete search history.

(56) References Cited

U.S. PATENT DOCUMENTS

| | | |
|---|---|---|
| 5,434,049 A | 7/1995 | Okano et al. |
| 5,804,684 A | 9/1998 | Su |
| 5,807,527 A | 9/1998 | Burgoyne |
| 7,589,184 B2 | 9/2009 | Hogan et al. |
| 9,534,214 B2 * | 1/2017 | Li .................. C12N 15/1006 |
| 2004/0101895 A1 | 5/2004 | Fomovskaia et al. |
| 2005/0208510 A1 | 9/2005 | Latham et al. |
| 2006/0014177 A1 | 1/2006 | Hogan et al. |

(Continued)

FOREIGN PATENT DOCUMENTS

| | | | |
|---|---|---|---|
| EP | 1036082 | * | 5/2002 |
| WO | 2011080160 A1 | | 7/2011 |

OTHER PUBLICATIONS

Virendra Kumar et al., "Preparation of an Anion-Exchange Adsorbent by the Radiation-Induced Grafting of Vinylbenzyltrimethylammonium Chloride Onto Cotton Cellulose and its Application for Protein Adsorption", Journal of Applied Polymer Science, pp. 5512-5521, vol. 102, Issue 6, Dec. 15, 2006.

(Continued)

*Primary Examiner* — Jezia Riley
(74) *Attorney, Agent, or Firm* — Pabitra K. Chakrabarti (57) ABSTRACT

A solid substrate for biological sample storage under dry-state and elution of biomolecules is provided. The dry, solid substrate comprises a surface modified with a plurality of hydrophilic groups; and the substrate is comprised of one or more protein denaturing agents impregnated therein under a substantially dry state. A method for elution of biomolecules from biological samples is also provided. The compositions disclosed herein provide for enhanced elution and recovery of biomolecules, such as nucleic acids, from the sample. The sample is disposed on a substrate, dried to a substantially dry state; eluted from the biological sample dried on the substrate by rehydrating the substrate in an elution buffer.

24 Claims, 1 Drawing Sheet

(56) References Cited

U.S. PATENT DOCUMENTS

| | | |
|---|---|---|
| 2009/0048439 A1 | 2/2009 | Weisburg et al. |
| 2011/0071031 A1 | 3/2011 | Khripin et al. |
| 2011/0081363 A1* | 4/2011 | Whitney ............ A01N 1/00 424/184.1 |
| 2012/0197009 A1 | 8/2012 | Baker |
| 2012/0289690 A1 | 11/2012 | Page et al. |
| 2013/0171026 A1 | 7/2013 | Li et al. |

OTHER PUBLICATIONS

Wolfgramm et al., "Simplified Buccal DNA Extraction with FTA Elute Cards", Forensic Science International: Genetics, Elsevier, vol. No. 3, Issue No. 2, pp. 125-127, Mar. 1, 2009.

Johanson et al., "DNA Elution from Buccal Cells Stored on Whatman FTA Classic Cards Using a Modified Methanol Fixation Method", Biotechniques, vol. No. 46, Issue No. 4, pp. 309-311, Apr. 2009.

Miles et al., "Improved Elution of DNA from Whatman FTA Cards Using PrepGEM/ ForensicGEM Storage Card Extraction Kits", ZyGEM, Oct. 1, 2012.

Henniges et al., "Electron Beam Irradiation of Cellulosic Materials-Opportunities and Limitations", Materials, vol. No. 6, pp. 1584-1598, Apr. 29, 2013.

* cited by examiner

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
cgggaaaggc tgaccggctg          20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide -continued

<400> SEQUENCE: 2
gtcacccggc atcaggtgcg                                       20

SUBSTRATES AND ASSOCIATED METHODS FOR ELUTION OF NUCLEIC ACIDS

FEDERALLY SPONSORED RESEARCH & DEVELOPMENT

This invention was made with Government support under contract number (HR0011-11-C0127) awarded by the Defense Advanced Research Projects Agency. The Government has certain rights in the invention.

SEQUENCE LISTING

The application contains a Sequence Listing which has been submitted in ASCII format via EFS-Web and is hereby incorporated by reference in its entirety. Said ASCII copy, created on Oct. 23, 2013, is named 268763-1_SL.txt and is 667 bytes in size.

FIELD

The invention generally relates to modified substrates for the stabilization and effective elution of nucleic acids from dried biological samples. Methods for stabilization and elution of nucleic acids from a biological sample in a dry format are also described.

BACKGROUND

Dry-state biological sample storage and preservation is desired for various applications, such as analyte detection, sensing, forensic and diagnostic applications, genome sequencing, whole-genome amplification, and the like. Long-term storage, transport and archiving of bio-specimen on filter paper and other chemically modified matrices are well-known techniques for preserving different biomolecules, such as nucleic acids, peptides, and proteins for different downstream applications.

Existing methods for the extraction of biomolecules from a substrate generally employ the use of different types of aqueous and organic extraction solvents, which may have adverse effects on biomolecule stability or downstream usability. Methods are known for using temperature and pH for differential binding and selective release of biomolecules such as nucleic acids from solid substrate, for example, binding of nucleic acids at acidic pH and release at alkaline pH. Alternatively, very high temperature or alkaline pH or combinations of both may be used to release bound biomolecules from a substrate through denaturation. The mixed mode resins are also known for recovering a target compound from aqueous solution at high or low ionic strength, using change in pH. The use of extremes of various environmental factors, such as pH, temperature, and/or high salt concentrations for re-dissolving or eluting nucleic acids cause the nucleic acids, especially RNA, to denaturation or degradation. Other environmental factors, such as, pressure, chemical or enzymatic hydrolysis, or the presence of contaminants may also promote degradation of archived biomolecules such as DNA, RNA, or protein during collection and storage.

Furthermore, known techniques for eluting of biomolecules from solid substrates may result in comparatively low recovery. For example, purified nucleic acids applied to the solid substrate results low recovery as determined by quantitative real time polymerase chain reaction (PCR). The success of the downstream applications of isolated nucleic acids from a sample may depend on maintaining the integral structure and function of target biomolecules and the amount of biomolecules used for each application.

Accordingly, a simplified method and an appropriate solid substrate for collecting, storing and eluting biomolecules from a sample disposed on the substrate with greater recovery is needed. In addition, maintaining the structural and functional integrity of the eluted nucleic acids is highly desirable.

BRIEF DESCRIPTION

In one embodiment, a solid substrate for biological sample storage and elution comprises a surface modified with a plurality of hydrophilic groups, and one or more protein denaturing agents impregnated therein the substrate in a substantially dry state.

In another embodiment, a method for eluting biomolecules from a biological sample disposed on a solid substrate, comprises contacting the biological material to a substrate, wherein the substrate comprises a surface modified with a plurality of negatively charged groups at physiological pH grafted by e-beam modification, and a composition comprising a protein denaturant, a reducing agent and a buffer disposed on the surface; binding the biomolecule to the surface; washing the biomolecule bound to the surface; and eluting the biomolecule from the substrate surface.

In yet another embodiment, a method for elution of nucleic acids from a biological sample disposed on a solid and dry cellulose substrate, comprises contacting the biological material to the surface comprising a plurality of negatively charged groups grafted by e-beam modification, and a composition comprising a protein denaturant, a reducing agent and a buffer in a dry state to extract the nucleic acid disposed on the surface; reversibly binding the extracted nucleic acid on the e-beam modified negatively charged substrate surface; washing the nucleic acid bound surface; and eluting the nucleic acid from the e-beam modified negatively charged substrate surface.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The embodiments of the invention provide suitable matrices and methods for elution of nucleic acids, such as DNA. One or more embodiments of the invention relate to a nucleic acid extraction substrate, wherein the substrate is configured to collect, extract and store nucleic acids from a biological sample for a prolonged period within a single process step, followed by elution of the nucleic acids for use in various downstream applications. The substrate is configured to store nucleic acids in a substantially dry-state at ambient temperature and to elute the stored nucleic acids while preserving the integrity of the nucleic acids.

To more clearly and concisely describe the subject matter of the claimed invention, the following definitions are provided for specific terms, which are used in the following description and the appended claims. Throughout the specification, exemplification of specific terms should be considered as non-limiting examples.

The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Where necessary, ranges have been supplied, and those ranges are inclusive of all sub-ranges there between.

The term "nucleic acid" as referred to herein comprises all forms of DNA (e.g. genomic DNA, mtDNA) or RNA (e.g., mRNA, miRNA, rRNA, tRNA, piRNA, ncRNA), as well as recombinant RNA and DNA molecules or analogues of DNA or RNA generated using nucleotide analogues. The nucleic acids may be single stranded or double stranded. The nucleic acids may include the coding or non-coding strands. The term also comprises fragments of nucleic acids, such as naturally occurring RNA or DNA which may be recovered using the extraction methods disclosed. "Fragment" refers to a portion of a nucleic acid (e.g., RNA or DNA).

The term, "reducing agents" as referred to herein include any chemical species that provides electrons to another chemical species. A variety of reducing agents are known in the art. Exemplary reducing agents include dithiothreitol (DTT), 2-mercaptoethanol (2-ME), and tris(2-carboxyethyl) phosphine (TCEP). Moreover, any combination of these or other reducing agents may be used. In particular embodiments, the reducing agent is TCEP.

The term "buffer" as used herein includes, for example, 2-Amino-2-hydroxymethyl-propane-1,3-diol (Tris), 2-(N-morpholino) ethanesulfonic acid (MES), 3-(N-morpholino) propanesulfonic acid (MOPS), citrate buffers, 4-(2-hydroxyethyl)-1-piperazineethanesulfonic acid (HEPES), and phosphate buffers. This list of potential buffers is for illustrative purposes only. The pH of the buffer selected for use in the compositions and methods disclosed herein is typically acid-titrated in the range of 2 to 8.

One or more embodiments of a solid substrate for biological sample storage and elution, comprises a surface modified with a plurality of hydrophilic groups; and one or more protein denaturing agents impregnated therein the substrate in a substantially dry state.

In one or more embodiments, the hydrophilic groups comprise one or more negatively charged groups. The term "negatively charged group" as used herein refers to the surface charge of the substrate at physiological pH condition. The pH of the surface may be maintained at a physiological pH, or a pH between 2 to 8 using a buffer. The solid substrates used for storage and elution of nucleic acids, comprise a surface, which may be modified with a plurality of negatively charged groups. In some embodiments, the negatively charged group comprises a carboxylic group, a sulfonic group, a phosphate group or a combination thereof. In one embodiment, the plurality of negatively charged group comprises a carboxylic group. In one embodiment, the plurality of negatively charged group comprises a sulfonic group.

As noted, the solid substrates used for storage and elution of nucleic acids, comprise negatively charged groups, which may be grafted on the surface by e-beam modification. In one or more embodiments, the negatively charged groups are grafted on both sides of the substrate by e-beam modification. As the negatively charged groups are grafted on the substrate by e-beam modification, the surface-modification of the substrate creates a rehydratable substrate composition.

In some embodiments, the plurality of negatively charged groups are developed using one or more e-beam reactive compounds comprising a methacrylate, an acrylate, an acrylamide, a vinyl ketone, a styrenic, a vinyl ether, a vinyl-containing moiety, an allyl-containing moiety, a benzyl-based compound, a tertiary-carbon (CHR3)-based compound, and any combination of two or more of the above functional moieties. In some other embodiments, the e-beam reactive compound further comprises an ester, an aliphatic, an aromatic, a hydrophilic compound, a heteroaromatic compound, or any combination of two or more of the above linkages. In some embodiments, the negatively charged groups are covalently linked to the substrate surface.

The negatively charged groups may be grafted on the surface of the substrate by e-beam modification. The e-beam modified substrate is achieved by the "dipping" or "dip-coating" procedure. The substrate is generally submerged into a solution containing chemical compositions containing the e-beam reactive negatively charged groups. The coating of the substrate is followed by e-beam exposure. The e-beam exposed substrate is washed extensively with water, and then dry using any standard method. The methods accomplish incorporation of the negatively charged groups into the substrate. In some embodiments, the modified cellulose are then coated with nucleic acid stabilizing agents, such as inclusion of protein denaturing agents, reducing agents, chelating agents, free-radical scavengers, buffers or combinations thereof.

The term "substrate" is interchangeably used herein as "solid substrate", "porous substrate" or "negatively charged substrate". The term "solid substrate" as used herein refers to a non-water dissolvable material, which enables collection, extraction and storage of nucleic acids followed by elution without solubilizing the material using water or aqueous buffer.

The solid substrate includes, but is not limited to, materials such as cellulose, cellulose acetate, nitrocellulose, glass fibers or combinations thereof. In one embodiment, the substrate comprises cellulose. In one or more embodiments, the substrate is selected from a nitrocellulose membrane, a cellulose membrane, a cellulose acetate membrane, a regenerated cellulose membrane, a nitrocellulose mixed ester membranes, a polyethersulfone membrane, a nylon membrane, a polyolefin membrane, a polyester membrane, a polycarbonate membrane, a polypropylene membrane, a polyvinylidene difluoride membrane, a polyethylene membrane, a polystyrene membrane, a polyurethane membrane, a polyphenylene oxide membrane, a poly(tetrafluoroethylene-co-hexafluoropropylene) membrane, and any combination of two or more of the above membranes.

In some embodiments, the substrate is a porous cellulose membrane. In one embodiment, the solid substrate is a porous cellulose paper, such as a cellulose substrate from GE Healthcare Life Sciences (formerly Whatman™). In one example, the cellulose substrate comprises 903-cellulose, FTA™ or FTA™ Elute.

In one or more embodiments, the solid substrate comprises one or more protein denaturing agents in addition to the negatively charged groups in a substantially dry state. In other embodiments, the negatively charged solid substrate further comprises buffer reagents, reducing agents, and optionally free-radical scavengers in addition to protein denaturing agents in a dry state. The substrate may extract and preserve nucleic acids under dry conditions, wherein the dried nucleic acids may further be eluted from the substrate by re-hydrating with water or aqueous buffer. Use of a dry solid substrate for collecting, extracting, preserving and eluting a sample maintains the concentration of available analyses and reduces the issues related to sample degradation, wherein the intact nucleic acids may be eluted with greater ease from the negatively charged substrate.

As noted, in some embodiments, one or more protein denaturing agents are impregnated within the substrate under a substantially dry state. As used herein, the term "substantially dry state" refers to further drying the sample to have approximately less than 2% of water content. In one or more embodiments, the substrate comprises a protein denaturing agent, wherein the protein denaturing agents are selected form salts, detergents, chaotropes, amino acids or combinations thereof. Without intending to be limited to a particular protein denaturing agent, exemplary protein denaturing agents include guanidinium thiocyanate, guanidinium hydrochloride, sodium thiocyanate, potassium thiocyanate, arginine, sodium dodecyl sulfate (SDS), urea or a combination thereof. In some embodiments, the substrate comprises a protein denaturing agent that is selected from thiocyanate salts impregnated in a dry state. Exemplary thiocyanate salts include, but are not limited to, guanidinium thiocyanate, sodium thiocyanate, potassium thiocyanate or combinations thereof. In one embodiment, the substrate comprises guanidium thiocyanate as a protein denaturing agent.

The protein denaturing agent may further comprise a chaotrope or a detergent. Without intending to be limited to a particular denaturing agent, protein denaturing agents may be categorized as either weak denaturing agents or strong denaturing agents depending on their biophysical properties and ability to completely inhibit biological enzyme activity. In some embodiments, weak protein denaturing agents (e.g. detergent) may be used for lysing cells and disrupting protein-protein interactions without denaturing nucleic acids. In further embodiments, use of strong protein denaturing agents (e.g. chaotrope) may also denature nucleic acid secondary structure in addition to denaturing cells and proteins. Numerous protein denaturing agents are known in the art and may be selected for use in the compositions and methods described herein.

Exemplary detergents may be categorized as ionic detergents, non-ionic detergents, or zwitterionic detergents. The ionic detergent may comprise anionic detergent such as, sodium dodecyl sulfate (SDS) or cationic detergent, such as ethyl trimethyl ammonium bromide. Non-limiting examples of non-ionic detergent for cell lysis include TritonX-100, NP-40, Brij 35, Tween 20, Octyl glucoside, Octyl thioglucoside or digitonin. Some zwitterionic detergents may comprise 3-[(3-Cholamidopropyl)dimethylammonio]-1-propanesulfonate (CHAPS) and 3-[(3-Cholamidopropyl)dimethylammonio]-2-hydroxy-1-propanesulfonate (CHAPSO). In some other embodiments, the protein denaturing agent may be selected from guanidinium hydrochloride, arginine, sodium dodecyl sulfate (SDS), urea, or combinations thereof. In some embodiments, the impregnated reagents comprise lytic reagents, nucleic acid-stabilizing reagents, nucleic acid storage chemicals and combinations thereof.

The substrate may further comprise a reducing agent, a buffer or combinations thereof impregnated therein under a dry state. The reducing agent may include dithiothreitol (DTT), 2-mercaptoethanol (2-ME), tris(2-carboxyethyl) phosphine (TCEP) or combinations thereof.

In some embodiments, the substrate comprises buffer reagents in a dry-state, which may be re-hydrated during sample collection and elution. As noted, the buffer-reagents provide a pH upon hydration which stabilizes the extracted nucleic acids, wherein the hydration may be achieved by adding a sample, water or any other solution (e.g. a buffer solution). The buffer provides physiological pH on hydration.

As noted, the substrate further comprises a buffer, wherein the buffer may be selected from 2-Amino-2-hydroxymethyl-propane-1,3-diol (Tris), 2-(N-morpholino) ethanesulfonic acid (MES), 3-(N-morpholino) propanesulfonic acid (MOPS), citrate buffers, 4-(2-hydroxyethyl)-1-piperazineethanesulfonic acid (HEPES), phosphate buffers or combinations thereof. The substrate generally maintains a neutral pH during elution of the nucleic acids. In some embodiments, the pH of the substrate is maintained between 4 and 8.

In one embodiment, the substrate is impregnated with nucleic acid stabilizing reagents. These stabilizing reagents may include DNAse or RNAse inhibitors, buffer reagents, or chelating agents (e.g., EDTA). As noted, the substrate further comprises a chelating agent, wherein the chelating agent is selected from ethylenediaminetetraacetic acid (EDTA), citric acid, ethylene glycol tetraacetic acid (EGTA) or combinations thereof. As noted, the substrate further comprises an RNase inhibitor, wherein the RNase inhibitor comprises vanadyl ribonucleoside complex (VRC), a nucleotide analogue, a commercially available RNase inhibitor (e.g., SUPERase-In™), or a triphosphate salts, such as sodium triphosphate.

The substrate may further comprise a UV protectant, a free-radical scavenger, a chelator or combinations thereof. Without intending to be limited to any specific UV protect, an exemplary antioxidants include, for example, hydroquinone monomethyl ether (MEHQ), hydroquinone (HQ), toluhydroquinone (THQ), uric acid, and ascorbic acid. In some embodiments, the antioxidant is THQ.

As noted, the solid substrate for biological sample storage and elution refers that the solid substrate is configured for biological sample storage and elution. The term "configured for" is referred to herein as the structure or composition of the substrate that enables the substrate to collect, extract, and store nucleic acids followed by elution. The term "storage" is used herein with respect to maintaining the extracted nucleic acids in a format suitable for further analysis.

In some embodiments, the solid substrate for biological sample storage and elution is a solid phase extraction substrate, which is coated with a plurality of negatively charged groups. A substrate, where the solid phase extraction method is used, is referred to herein as a solid phase extraction substrate. Solid-phase extraction (SPE) technology has been leveraged to reduce the extraction times of high purity nucleic acids for sequencing and other applications. The solid phase extraction is an extraction method that uses a solid phase and a liquid phase to isolate one or more molecules of the same type, or different types, from a material. The solid phase extraction substrate is used, for example, to purify a sample upstream of a chromatographic or other analytical method. One example of the method comprises loading a sample (e.g. a biological sample) onto the saccharide coated solid phase extraction substrate, storing the substrate at ambient temperature to achieve a substantially dry state, and rehydrating the substrate with a suitable buffer to elute nucleic acids from the substrate.

The plurality of negatively charged groups on the substrate of the present invention provides enhanced release and recovery of nucleic acids during an elution process. The negatively charged substrate for releasing nucleic acid is especially useful during elution of nucleic acids from a less quantity of sample disposed on the substrate. The elution of nucleic acids from a negatively charged substrate avoids the need to use high ionic strength or alkaline pH buffers for elution and subsequent dilution of the eluted nucleic acids to adjust the ionic strength and pH required for the downstream applications. As a consequence, any loss of nucleic acids through further sample-dilution or reduced recovery due to degradation, denaturation or dilution of small amounts of nucleic acid may be avoided. Use of a negatively charged substrate is advantageous when the nucleic acid of interest is present in a sample at a low copy number and for use with certain detection and/or amplification methods, wherein the negatively charged substrate enables elution of nucleic acids with greater ease and high yield.

In some embodiments, the negatively charged substrate reduces the risk of leaching chemicals from a chemically modified substrate with the eluted nucleic acids, which can otherwise lead to significant problems, specifically if the resultant product is used in polymerase chain reaction (PCR).

In some embodiments, the dried reagents impregnated in the substrate are hydrated by adding a buffer, water or a biological sample. In some embodiments, water or buffer is added to hydrate the substrate and reconstitute or activate the reagents embedded in the substrate. In some embodiments, the hydration of the substrate may result in reconstituting the reagents impregnated in the substrate.

An example of a method for eluting biomolecules from a biological sample disposed on a substrate comprises contacting the biological material to the substrate, wherein the substrate comprises a surface modified with a plurality of negatively charged groups grafted by e-beam modification, and a composition comprising a protein denaturant, a reducing agent and a buffer disposed on the surface. The method further comprises binding the biomolecule to the surface, washing the biomolecule bound to the surface and eluting the biomolecule from the substrate surface. In some embodiments, the biological sample is drying to a substantially dry state and eluting the biomolecule from the dried biological sample on the substrate by rehydrating the substrate in an elution buffer.

As noted, in some embodiments, the method comprises contacting the biological sample to the negatively charged substrate, wherein the non-limiting examples of the term "contacting" include, applying a sample to the substrate or disposing a sample to the substrate using a pipet, catheter, syringe or conduit or by using a robotic for multiple samples. The sample may be poured on the substrate manually from a tube or a vial. Contacting a biological sample comprising cells to the substrate results in cell lysis which releases nucleic acids, for example by using negatively charged FTA™ Elute cellulose papers, wherein the modified FTA™ Elute cellulose papers may enable efficient elution of the nucleic acids. Nucleic acids, such as DNA or RNA may be extracted from cells disposed on the negatively charged substrate via cell-lysis, such as by evaporative cell-lysis or cell lysis upon action of lysis reagents, for example, using impregnated lysis reagents.

As noted, the method comprises binding of the biomolecules to the negatively charged surface of the substrate, wherein the binding may be achieved by incubating the biological sample on the substrate for few minutes. Incubation of the sample on the substrate allows the biological sample comprising the biomolecules to reside on the surface of the substrate, which enhances binding of the biomolecules on the surface of the substrate. The binding of the negatively charged biomolecules, such as nucleic acids to the negatively charged substrate is possible for the coating disposed on the surface of the substrate. The coating may comprise a composition comprising nucleic acid stabilizing materials, such as protein denaturing agents, reducing agents, chelating agents or free-radical scavengers. The nucleic acid stabilizing composition enables the biomolecules to bind to the substrate surface. The binding of the biomolecules on the surface of the substrate also enhances by drying the biological sample on the substrate.

As noted, in some embodiments, the method comprises drying the biological sample to a substantially dry state, wherein the term "substantially dry state" refers to drying the sample to have approximately less than 2% of water content. In one or more embodiments, the drying of the biological sample is achieved by evaporation of the liquid from the sample. In some embodiments, the biological sample is dried by desiccation of the sample. In some other embodiments, the biological sample is dried using a room temperature or elevated-temperature air-drying of the sample, which leaves the biomolecules of the biological sample intact. The drying process is selected such that the process does not affect the structure or function of the biomolecules of the biological sample.

As noted, in some embodiments, the method further comprises eluting the biomolecules from the surface of the substrate. The term "elution" refers to any method for releasing the biomolecules, such as nucleic acids from the substrate, wherein the nucleic acids are isolated from a biological sample. To recover preserved nucleic acids on the cellulose based materials, such as 31-ETF, 903, FTA classic, FTA Elute or other substrates employed either flow through elution or punch incubation in buffers. Without ascribing to a particular hypothesis, the negatively charged groups on the substrate, more specifically at the cellulosic substrate, may increase the repulsion of the similarly charged nucleic acids, resulting in better release of the nucleic acids during rehydration and elution of the sample.

An example of a method for eluting the stored nucleic acids from a sample comprises the steps of adding water or buffer solution onto a negatively charged solid substrate. In some embodiments, the elution of nucleic acids from the biological sample is achieved upon hydration of the negatively charged solid substrate under an elevated temperature. Any method that is suitable for elution of the nucleic acids may be employed for eluting the extracted and/or stored nucleic acids from a negatively charged solid substrate. One or more embodiments of the method comprise recovering nucleic acids from the negatively charged substrate by solid phase extraction technique. In one or more embodiments, the nucleic acids are recovered by rehydrating the solid substrate in an aqueous solution, a buffer, or an organic solution and wherein the nucleic acids are subjected to further analysis. In one example embodiment, the nucleic acids are recovered by rehydrating the cellulose paper using an aqueous solution. In some embodiments, the nucleic acids are recovered from the solid substrate by electroelution. In some embodiments, the nucleic acids are recovered by rehydrating the cellulose paper comprising negatively charged groups and one or more protein denaturing agents comprising thiocyanate salt, using water or a buffer.

In one or more embodiments, the term "elution buffer" refers to aqueous solutions that are commonly used for eluting nucleic acids in the art. Without intending to be limited to any specific elution buffers, the elution buffers may include water, tris(hydroxymethyl)aminomethane ethylenediaminetetraacetic acid (Tris-EDTA or TE), 4-(2-hydroxyethyl)-1-piperazineethanesulfonic acid (HEPES), and the like. In some embodiments, the elution buffer comprises proteinase K.

The method delineated above may optionally include a step of washing the substrate before recovering the nucleic acids from the solid substrate for further analysis. In one or more embodiments, the method comprises washing of the bound biomolecules to the substrate. The washing may remove any non-specifically bound biomolecules to the substrate. The washing may also remove any non-specifically bound impurities to the substrate. For example, the washing step may remove any impurities present in the extracted and/or stored nucleic acids. In some embodiments, the washing may be performed repeatedly, in some other embodiments; the washing may be performed once or twice. For example, the substrate may be washed for one or more times with a suitable wash buffer or water prior to recovery of the nucleic acids. The number of wash depends on the use of eluted biomolecules for different downstream applications.

The biological sample may comprise one or more biomolecules. In one or more embodiments, the biomolecule comprises a protein, a peptide or a nucleic acid. The extracted nucleic acids comprise ribonucleic acids (RNA), deoxy ribonucleic acids (DNA), peptide nucleic acids (PNA) or a combination thereof. In one embodiment, the extracted nucleic acids comprise DNA. The DNA may be genomic DNA or mtDNA. In one embodiment, the extracted nucleic acids comprise RNA. The RNA may be mRNA, tRNA, rRNA, small RNA, siRNA, miRNA, non-coding RNA, animal RNA, plant RNA, viral RNA or bacterial RNA.

The samples utilized in this method include, but are not limited to, biological samples such as blood, serum, tissue, and saliva obtained from any organism, including a human. Biological samples may be obtained by an individual undergoing a self-diagnostic test (e.g., blood glucose monitoring) or by a trained medical professional through a variety of techniques including, for example, aspirating blood using a needle or scraping or swabbing a particular area, such as a lesion on a patient's skin. Methods for collecting various biological samples are well known in the art. The term "sample" includes biological samples as defined above, but also includes, for example, tissue cultured cells and purified nucleic acids.

EXAMPLE

Reagents: 31-ETF and Ficoll PM 400 were from GE Healthcare Life Sciences. Guanidinium thiocyanate, trehalose, melezitose, carboxymethyl cellulose, dextran, raffinose, alginic acid, glucosamine, chitosan, gluconic acid, amylopectin, chitosan oligosaccharide lactine, sorbitan monopalmitate, and polyvinyl alcohol were all purchased from Sigma-Aldrich (MO, USA).

Example 1

Recovery of DNA Using Substrates Modified with Acrylic Acid

Substrate preparation—modified cellulose substrates were prepared using the scheme 1 below. The cellulose substrates were reacted with acrylic acid, in presence of electron beam (e-beam) irradiation, resulted in acrylic acid (AA) modified cellulose or cellulose-AA. The substrate further comprises basic dope formulation comprising 3-(N-morpholino) propanesulfonic acid (MOPS), guanidinium thiocyanate (GuSCN), tris(2-carboxyethyl)phosphine (TCEP) and toluhydroquinone (THQ).

Scheme 1:

The e-beam modified cellulose substrates were then coated with nucleic acid stabilizing formulations listed in the table 1 below. 31-ETF cellulose substrates were then dipped into each of the coating solutions, forced through a nip roller, and then dried at 150° C. in an oven with air flow.

TABLE 1

Composition of nucleic acid stabilizing coating on the cellulose substrate:

| | | Basic dope formulation, mg/ml | | | |
|---|---|---|---|---|---|
| Sample | Substrate | MOPS | GuSCN | TCEP | THQ |
| E1.1 | Cellulose | 20 | 50 | 10 | 5 |
| E1.4 | Cellulose-AA | 20 | 50 | 10 | 5 |

1 ng of HindIII digested Lambda DNA (DNA digest) dissolved in 5 μl TE. Onto the surface modified 31ETF cellulose substrate (E 1.1, E 1.4) prepared from Table 1, the DNA samples were applied on the substrate and dried. The substrates were E 1.1, comprising GuSCN as control and E1.4 comprising GuSCN and AA-20. The samples were dried on the substrate overnight with desiccation at room temperature. The DNA was eluted by flowing 35 μl HET buffer (20 mM Hepes, 0.1 mM EDTA, 0.01% Tween-20, pH 8) through the paper at 10 μl/min. Before flow elution, the substrate was pre-wet with the same buffer for 1 minute.

The eluted samples were subjected to qPCR. 2 μl of eluted DNA sample (⅕sth vol.) was added to the 30 μl of reaction volume, in presence of forward primer (SEQ. ID. NO. 1: 5'-CGG GAA AGG CTG ACC GGC TG-3') and reverse primer (SEQ. ID. NO. 2: 5'-GTC ACC CGG CAT CAG GTG CG-3') specific to the 23.1 kb fragment of the DNA digest.

Figure 1:
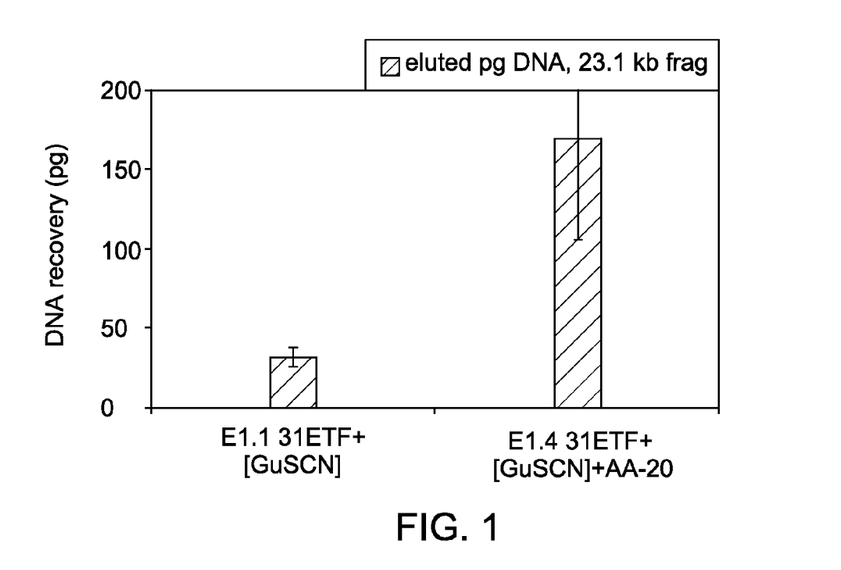
FIG. 1 is a graph comparing DNA recovery from acrylic acid-coated e-beam modified cellulose substrates relative to a control formulation comprising FTA™ Elute.

The results of Example 1 are set forth in FIG. 1. FIG. 1 illustrates the change in DNA recovery from dried DNA sample spot, normalized to a control formulation (sample E.1.1 of table 1) comprising GuSCN. Higher relative DNA recovery was observed from sample loaded to E 1.4, 31-ETF-cellulose substrate modified with AA-20, as shown in FIG. 1.

Example 2

Recovery of DNA Using Substrates Modified with Vinyl Sulfonic Acid

Substrate preparation—modified cellulose substrates were prepared using the scheme 2 below. The cellulose substrates were reacted with vinylsulfonic acid, in presence of e-beam exposure, resulted in sulfonic acid (SA) modified cellulose or cellulose-SA. The substrate further comprises basic dope formulation comprising MOPS, GuSCN, TCEP and THQ.

Scheme 2:

The e-beam modified cellulose substrates were then coated with nucleic acid stabilizing formulations listed in the table 1 below. 31-ETF cellulose substrates were then dipped into each of the coating solutions, forced through a nip roller, and then dried at 150° C. in an oven with air flow.

TABLE 2

Composition of nucleic acid stabilizing coating on the cellulose substrate:

| Sample | Substrate | Basic dope formulation, mg/ml | | | |
|---|---|---|---|---|---|
| | | MOPS | GuSCN | TCEP | THQ |
| E2.1 | Cellulose | 20 | 50 | 10 | 5 |
| E2.2 | Cellulose-SA | 20 | 50 | 10 | 5 |

1 ng of HindIII digested Lambda DNA (DNA digest) dissolved in 5 μl of model mucus (M1, 110 mM NaCl, 30 mM KCl, 40 μM Ascorbic Acid, 40 μM Glutathione, 10 μM BSA, 3% Mucin type II (from porcine stomach), 25 mM EDTA). Onto the surface modified 31ETF cellulose substrate (E 2.1, E 2.2) prepared from Table 1, the DNA samples were applied and dried. The substrates were E 2.1, comprising GuSCN as control and E2.2 comprising GuSCN and SA-20. The samples were dried on the substrate for 5 minutes at room temperature. 3 mm punches were taken from the dried sample. The punches were shaken in elution buffer of 50 μl HET at 750 rpm for 40 minutes at 45° C., and 20 μL of the resulting supernatant was recovered and precipitated using a DNA Extractor SP kit (Wako).

The eluted samples were subjected to qPCR. 2 μl of eluted DNA sample (1/25th vol.) was added to the 30 μl of reaction volume, in presence of forward primer (SEQ. ID. NO. 1: 5'-CGG GAA AGG CTG ACC GGC TG-3') and reverse primer (SEQ. ID. NO. 2: 5'-GTC ACC CGG CAT CAG GTG CG-3') specific to the 23.1 kb fragment of the DNA digest.

Figure 2:
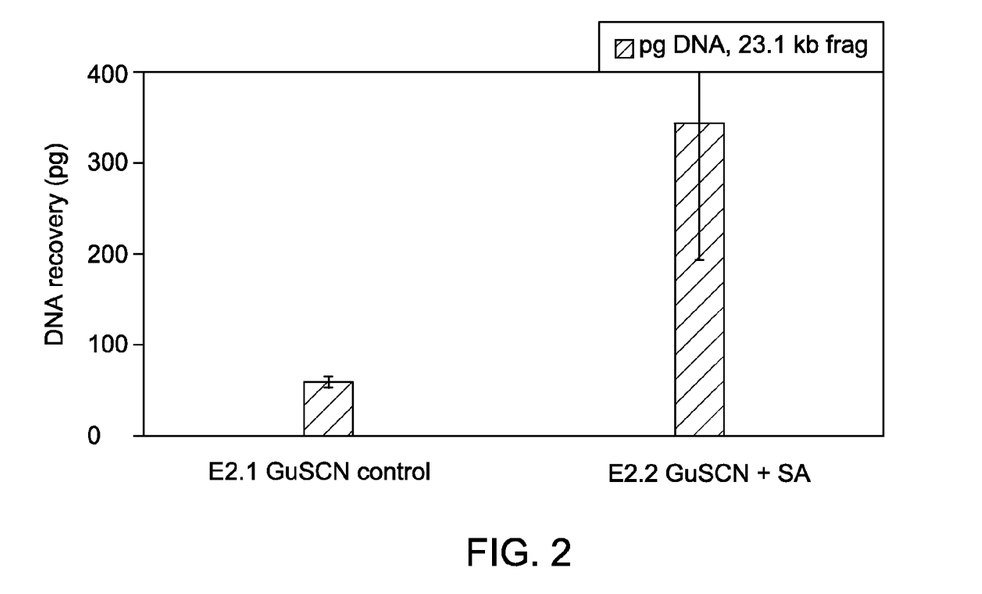
FIG. 2 is a graph comparing DNA recovery from vinylsulfonic acid-coated e-beam modified cellulose substrates relative to a control formulation comprising FTA™ Elute.

The results of Example 2 are set forth in FIG. 2. FIG. 2 illustrates the change in DNA recovery from dried DNA sample spot, normalized to a control formulation (sample E.2.1 of table 2) comprising GuSCN. Higher relative DNA recovery was observed from sample loaded to E 2.2, 31-ETF-cellulose substrate modified with SA-20, as shown in FIG. 2.

While only certain features of the invention have been illustrated and described herein, many modifications and changes will occur to those skilled in the art. It is, therefore, to be understood that the appended claims are intended to cover all such modifications and changes as fall within the scope of the invention.

---

The invention claimed is:
1. A solid substrate for eluting biomolecules from a biological sample, consisting essentially of:
   a cellulose membrane;
   a plurality of hydrophilic negatively charged groups covalently linked to a surface of the cellulose membrane; and
   one or more protein denaturing agents impregnated in the cellulose membrane under a substantially dry state;
   wherein the solid substrate is a non-water dissolvable substrate.
2. The substrate of claim 1, wherein the plurality of hydrophilic negatively charged groups comprises a carboxylic group, a sulfonic group, a phosphate group, or combinations thereof.
3. The substrate of claim 2, wherein the plurality of negatively charged groups comprise a carboxylic acid or carboxylate group.
4. The substrate of claim 2, wherein the plurality of hydrophilic negatively charged groups comprises a sulfonic acid or sulfonate group.
5. The substrate of claim 2, wherein the plurality of hydrophilic negatively charged groups is developed using one or more e-beam reactive compounds comprising a methacrylate, an acrylate, an acrylamide, a vinyl ketone, a styrenic, a vinyl ether, a vinyl-containing moiety, an allyl-containing moiety, a benzyl-based compound, a tertiary-carbon (CHR3)-based compound, and any combination of two or more of the said functional moieties.
6. The substrate of claim 5, wherein the e-beam reactive compound further comprises an ester, an aliphatic, an aromatic, a hydrophilic compound, a hetero-aromatic compound, or any combination of two or more of the said linkages.
7. The substrate of claim 1, wherein the substrate further comprises a reducing agent, a buffer, a chelating agent, an anti-oxidant or combinations thereof.
8. The substrate of claim 1, wherein the protein denaturing agents are selected from guanidinium thiocyanate, guanidinium hydrochloride, arginine, and sodium dodecyl sulfate (SDS), urea, and combinations thereof.
9. The substrate of claim 7, wherein the reducing agent is selected from the group consisting of dithiothreitol (DTT), 2-mercaptoethanol (2-ME), and tris(2-carboxyethyl)phosphine (TCEP), and combinations thereof.
10. The substrate of claim 7, wherein the buffer is selected from the group consisting of 2-Amino-2-hydroxymethyl-propane-1,3-diol (Tris), 2-(N-morpholino) ethanesulfonic acid (MES), 3-(N-morpholino) propanesulfonic acid (MOPS), citrate buffers, 4-(2-hydroxyethyl)-1-piperazineethanesulfonic acid (HEPES), phosphate buffers, and combinations thereof.
11. The substrate of claim 7, wherein the chelating agent is selected from the group consisting of ethylenediaminetetraacetic acid (EDTA), citric acid, ethylene glycol tetraacetic acid (EGTA), and combinations thereof.
12. The substrate of claim 7, wherein the anti-oxidant is selected from the group consisting of hydroquinone monomethyl ether (MEHQ), hydroquinone (HQ), toluhydroquinone (THQ), ascorbic acid, uric acid, and combinations thereof.
13. The substrate of claim 1, wherein the substrate is configured to elute one or more biomolecules from the biological sample.
14. The substrate of claim 13, wherein the one or more biomolecules comprise a protein, peptide or a nucleic acid.
15. The substrate of claim 13, wherein the one or more biomolecules are nucleic acids comprising DNA.
16. A method for eluting a biomolecule from a biological material disposed on a substrate, comprising:
   contacting the biological material to a substrate, wherein the substrate is a non-water dissolvable substrate consisting essentially of cellulose membrane a plurality of negatively charged groups covalently linked to a surface of the cellulose membrane to form a modified surface, and a composition comprising a protein denaturant, a reducing agent and a buffer impregnated in the cellulose membrane;
   binding the biomolecule to the modified surface of the cellulose membrane to form biomolecule-bound modified surface;
   washing the biomolecule of the biomolecule-bound modified surface; and
   eluting the biomolecule from the biomolecule-bound modified surface.
17. The method of claim 16, wherein the biomolecule binds to the modified surface by non-covalent interaction.
18. The method of claim 16, further comprising washing the biomolecule of the biomolecule-bound modified surface with a wash buffer.
19. The method of claim 16, wherein the biomolecule is eluted from the biomolecule-bound modified surface by using an elution buffer.
20. The method of claim 16, wherein the plurality of negatively charged groups comprise a carboxylic group, a sulfonic group, a phosphate group, or any combination thereof.
21. The method of claim 16, wherein the plurality of negatively charged groups comprises a carboxylic group or a sulfonic group.
22. The method of claim 16, wherein the biomolecule comprises a protein, peptide or a nucleic acid.
23. The method of claim 16, wherein the biomolecule is a nucleic acid comprising DNA.
24. A method for elution of a nucleic acid from a biological material disposed on a surface of a non-water dissolvable cellulose substrate, comprising:
   contacting the biological material to the substrate surface consisting essentially of a plurality of hydrophilic negatively charged groups covalently linked to the substrate surface, and then contacting the substrate with a composition comprising a protein denaturant, a reducing agent and a buffer in a dry state to extract the nucleic acid disposed on the surface;
   reversibly binding the extracted nucleic acid on the negatively charged substrate surface;
   washing the nucleic acid bound surface; and eluting the nucleic acid from the negatively charged substrate surface.

\* \* \* \* \*